US012108931B2

(12) United States Patent
Inglis (10) Patent No.: US 12,108,931 B2
(45) Date of Patent: Oct. 8, 2024

(54) MEDICAL DEVICE IMAGING SYSTEMS AND METHODS

(71) Applicant: COVIDIEN LP, Mansfield, MA (US)

(72) Inventor: Peter Douglas Colin Inglis, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 332 days.

(21) Appl. No.: 17/476,744

(22) Filed: Sep. 16, 2021

(65) Prior Publication Data

US 2022/0110504 A1 Apr. 14, 2022

Related U.S. Application Data

(60) Provisional application No. 63/091,693, filed on Oct. 14, 2020.

(51) Int. Cl.
| | |
|---|---|
| *A61B 1/00* | (2006.01) |
| *A61B 1/267* | (2006.01) |
| *G06V 20/64* | (2022.01) |
| *H04N 23/51* | (2023.01) |
| *H04N 23/53* | (2023.01) |

(52) U.S. Cl.
CPC ........ *A61B 1/0005* (2013.01); *A61B 1/00009* (2013.01); *A61B 1/00016* (2013.01); *A61B 1/267* (2013.01); *G06V 20/64* (2022.01); *H04N 23/51* (2023.01); *H04N 23/53* (2023.01)

(58) Field of Classification Search
CPC ... A61B 1/0005; A61B 1/00052; A61B 1/267; H04N 23/53
See application file for complete search history.

(56) References Cited

U.S. PATENT DOCUMENTS

| | | | |
|---|---|---|---|
| 9,302,061 B2 | 4/2016 | Jafari et al. | |
| 2008/0091064 A1* | 4/2008 | Laser | A61B 1/00108 600/179 |
| 2009/0198111 A1* | 8/2009 | Nearman | A61B 5/6898 901/30 |
| 2010/0261968 A1* | 10/2010 | Nearman | A61B 1/0004 600/196 |
| 2011/0137127 A1* | 6/2011 | Schwartz | A61B 1/05 600/188 |

(Continued)

FOREIGN PATENT DOCUMENTS

| | | |
|---|---|---|
| EP | 3 107 474 A1 | 12/2016 |
| WO | 2022/133248 A1 | 6/2022 |
| WO | 2022/266500 A1 | 12/2022 |

OTHER PUBLICATIONS

International Search Report for International Application No. PCT/US2021/051060 mailed Dec. 10, 2021 (12 pages).

*Primary Examiner* — Ellen C Hammond
*Assistant Examiner* — Holly Joanna Lane (57) ABSTRACT

A time-synchronized video imaging system includes an environmental camera that acquires environmental images of a patient while a video laryngoscope acquires airway images of the patient. A monitor receives the airway images from the video laryngoscope and the environmental images from the environmental camera. The monitor time-synchronizes the airway images and the environmental images to each other to generate a combined view video file of the time-synchronized airway images and environmental images to permit review of macro or environmental effects on a patient intubation.

20 Claims, 9 Drawing Sheets

(56) References Cited

U.S. PATENT DOCUMENTS

| | | | |
|---|---|---|---|
| 2017/0326332 A1* | 11/2017 | Giap | G06T 19/006 |
| 2019/0133430 A1* | 5/2019 | Inglis | A61B 1/00016 |
| 2019/0142262 A1 | 5/2019 | Colin et al. | |
| 2019/0282324 A1* | 9/2019 | Freeman | A61M 16/0084 |
| 2020/0254204 A1 | 8/2020 | Moffat et al. | |

* cited by examiner

MEDICAL DEVICE IMAGING SYSTEMS AND METHODS

CROSS-REFERENCE TO RELATED APPLICATION

The present application claims priority to and the benefit of U.S. Provisional Application No. 63/091,693, entitled "MEDICAL DEVICE IMAGING SYSTEMS AND METHODS" and filed Oct. 14, 2020, the disclosure of which is hereby incorporated by reference in its entirety for all purposes.

BACKGROUND

The present disclosure relates generally to medical devices and, more particularly, to medical device imaging systems and methods.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, tracheal tubes may be used to control the flow of air or other gases through a patient's trachea and into the lungs, for example during mechanical ventilation. Such tracheal tubes may include endotracheal tubes, tracheostomy tubes, or transtracheal tubes. Laryngoscopes are in common use during intubation (the insertion of an endotracheal tube into the trachea of a patient).

The video laryngoscope is a form of indirect laryngoscopy in which a medical professional (such as a doctor, therapist, nurse, or other practitioner) views a video image of the patient's larynx on a display screen. A video laryngoscope may include an integral display that is in the line-of-sight of the laryngoscope operator so that the patient airway is viewable on the display screen in real-time to facilitate navigation and insertion of tracheal tubes within the airway.

SUMMARY

Certain embodiments are summarized below. These embodiments are not intended to limit the scope of the disclosure. Indeed, the present disclosure may encompass a variety of forms that may be similar to or different from the embodiments set forth below In one embodiment, a video imaging system is provided that includes a monitor comprising a display screen. A video laryngoscope of the video imaging system includes a camera that acquires airway images of a patient. An environmental camera of the video imaging system acquires environmental images of a patient environment. The monitor of the video imaging system operates to receive the airway images from the video laryngoscope and the environmental images from the environmental camera; synchronize the airway images and the environmental images to each other; and combine the synchronized airway and environmental images into a combined video file.

In one embodiment, a medical device system includes a video laryngoscope that acquires airway images of a patient and an environmental camera that acquires environmental images. A monitor of the system operates to receive the airway images from the video laryngoscope; receive the environmental images from the environmental camera; determine a first time difference between a monitor clock and a video laryngoscope clock, and a second time difference between the monitor clock and an environmental camera clock; shift the airway images relative to the environmental images based on the first and second differences, to time-synchronize the airway images and the environmental images to each other; and generate a video file comprising the time-synchronized airway images and environmental images.

In one embodiment, a method includes the steps of receiving, at a monitor, airway images and laryngoscope clock information from a video laryngoscope; acquiring, by the monitor, environmental images from a room-facing environmental camera on the monitor, wherein the environmental images are acquired simultaneously with the airway images; determining a relative time difference between the laryngoscope clock information and a monitor clock information; time-synchronizing the airway images and the environmental images based on the relative time difference; and generating a composite view video file with a combined view of the time-synchronized airway images and environmental images.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

A medical professional may use a laryngoscope to view a patient's oral cavity to facilitate insertion of a tracheal tube (e.g., endotracheal tube, tracheostomy tube, or transtracheal tube) through the patient's oral or nasal cavity and into the patient's trachea as part of an intubation procedure. Video laryngoscopes include a camera on a portion of the laryngoscope that is inserted into the patient's oral cavity to obtain an image (e.g., still image and/or moving image, such as a video) of the oral cavity. The image may then be displayed during the intubation procedure to enable the medical professional to visualize the oral cavity and to facilitate manipulation and insertion of the tracheal tube. The video laryngoscope may include an integral display screen that is positioned in the line-of-sight of the laryngoscope operator but that may not be highly visible to other clinicians in the room. During operation of the video laryngoscope, the acquired images can be communicated, e.g., streamed in real-time (such as via a wireless connection) to a separate display screen that displays the video laryngoscope images to permit viewing by other clinicians. The separate display screen can be one or more display screens positioned in the procedure room or in a separate room (such as a staging room, nursing station, or other area). In this manner, the airway status of the patient is visible to other clinicians, who may view these images as part of training, to offer relevant information or advice to the laryngoscope operator, and/or to prepare for subsequent procedures based on the progress of the intubation. In one example, a surgical team in a staging area may move into position and prepare initial steps of a surgical procedure based on video laryngoscope images that are indicative of near-completion of an intubation. In another example, the laryngoscope operator can be advised of potential intubation difficulties based on the visible airway anatomy.

During an intubation, the images from the video laryngoscope are obtained from inside the patient (such as inside the patient's mouth or upper airway), and thus these images provide only a limited perspective of interventions being conducted on the patient, or other events taking place in the room. Events or interventions external to the patient are not necessarily evident in the video laryngoscope images obtained from inside the patient's mouth or airway. Such external or macro events or context may be patient movement (such as coughing, reflexes, or other movements), administration of sedation or other medication to the patient, restraint or positioning of the patient, concurrent medical events of the patient (such as emergency interventions, topical preparations, surgical incision and/or incision closing, individual stages of surgery, or others), technique of the laryngoscope operator, type of airway tube or other instrument being used, communications and interactions between clinicians in the patient environment, the presence and positioning, including arrivals or departures, of members of the medical team, status or arrangement of the room, changes to the room environment, and many others. In one example, an emergency intubation occurs while concurrent stabilization measures are being performed on the patient that jostle the patient and shift the position of the airway, which may extend the overall intubation time or increase a risk of esophageal intubation. Providing environmental context information, external to the patient, during an intubation procedure may provide training benefits to clinicians, better inform other members of the medical team, and augment the medical record for an individual patient.

Provided herein are techniques that align images acquired by a video laryngoscope with environmental images acquired by a room or other device camera showing contextual events during an intubation procedure. The techniques time-synchronize images from devices that are not time-synchronized to one another (e.g., different devices with respective clocks having different times). In certain embodiments, one or all of the devices in the system are also not set to a correct local time. In one embodiment, the system includes a video laryngoscope that acquires patient airway images and an environmental camera that simultaneously acquires environmental images from the procedure room. The airway images and environmental images are transmitted to a processor that combines the images into a dual-image, time-synchronized view. In an embodiment, the processor synchronizes the images to one another. For example, synchronization may include determining a time difference between a system clock on the processor and local clocks on each of the video laryngoscope and the environmental camera. The system uses these time differences to synchronize the environmental images with the airway images so they are both showing content that occurs at the same time. The processor renders a combined view (e.g., a video feed or a video file) that shows both video images playing together, so that the environmental context in the room can be seen alongside the progress of intubation inside the patient's airway. This combined view may be used in real-time during intubation, or may be used retrospectively after intubation to assess intubation success and improve clinical interventions and patient records. The disclosed techniques address device-specific challenges associated with evaluating images acquired from distributed medical devices that are not time-synchronized with each other. Further, the techniques to align these acquired images do not synchronize the clocks of the devices to one another (such as by updating or changing different clocks to be on the same time). Instead, images acquired from these devices are synchronized together based on differences in associated clock information from the respective devices. Thus, the techniques are directed to time-synchronization of images, without requiring synchronization of clocks on various distributed cameras, scopes, and devices.

While embodiments of the disclosure are discussed in the context of video laryngoscopes, it should be understood that the present techniques may be used in conjunction with other medical devices that acquire internal patient images, such as endoscopes or other types of internal scopes, to synchronize or time-align external environmental images with internal anatomical images. The disclosed techniques solve a technological computing and communication challenge associated with medical devices that are not operating on the same global/synchronized clock. For example, a peripheral medical device such as a video laryngoscope may be manufactured in a first time zone and then distributed globally to time zones all over the world. As a result, the internal clock of the medical device is not necessarily synchronized to local time, and certain medical devices may not be programmed to permit updating of the internal clock. Further, to reduce battery size, improve portability, or protect against cybersecurity vulnerability, some medical devices may have limited communication capacity that is not capable of receiving external synchronization commands. As a result, multiple devices in a system may have conflicting clock information. The present techniques address such cases to facilitate time-synchronization of images acquired by different devices.

Figure 1:
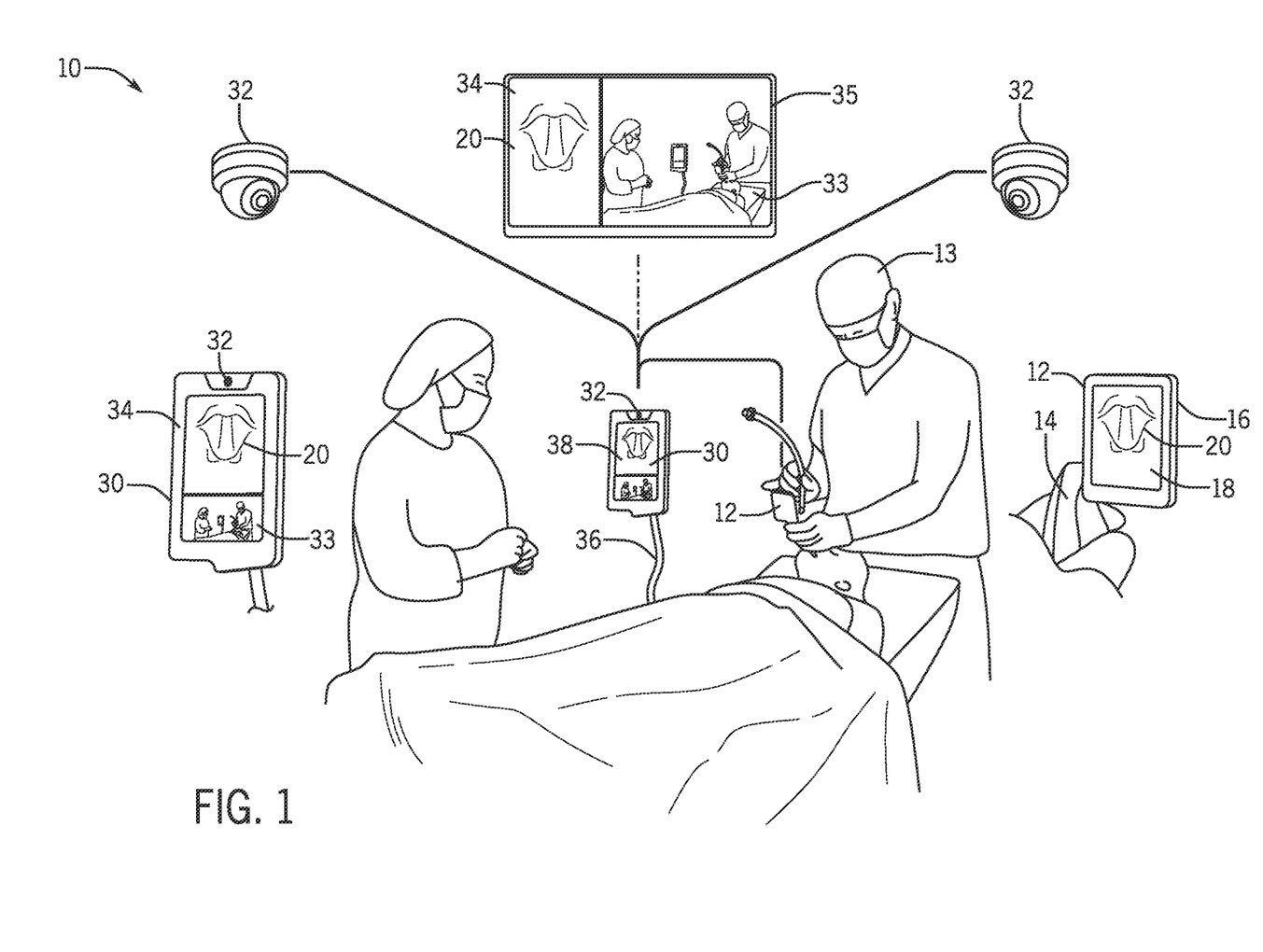
FIG. 1 is a schematic illustration of a patient environment including a video imaging system, in accordance with an embodiment of the present disclosure.

FIG. 1 is a schematic illustration of a patient environment that includes a video imaging system 10 that operates to synchronize airway images and environmental images of the patient environment and to generate a composite video file that has a combined view of the synchronized images. The patient environment can be any room where an intubation is being performed, such as a medical suite in a hospital or other care setting, an operating or other procedure room, patient recovery room, an emergency intubation setting, or other environments. The video imaging system 10 can include a video laryngoscope 12 that, in operation, is used for airway visualization of a patient. The video imaging system 10 may additionally or alternatively be used with other patient visualization instruments that acquire patient images, e.g., internal patient images.

A laryngoscope operator 13 holds a body 14 of the laryngoscope coupled to a display portion 16 having a display screen 18. Acquired airway images 20 are displayed on the display screen 18. The video laryngoscope 12 may be used as part of an intubation procedure to advance a tracheal tube into a patient airway to secure the airway for mechanical ventilation. Accordingly, the operator 13 of the video laryngoscope 12 performs the intubation and directly manipulates the endotracheal tube within the patient's airway, and other clinicians in the patient environment assist the laryngoscope operator, monitor a condition of the patient, prepare or adjust medical equipment in the patient environment, and/or wait until the airway is secured to perform other procedures or interventions.

These airway images 20 may also be stored in a memory (on the video laryngoscope 12 or on a separate memory device) and associated with a patient medical record. The acquired airway images 20 may reveal lesions, challenging airway anatomy, movement of an advancing tracheal tube and/or endoscope, improper esophageal intubation, and other factors that may affect patient care. These images can be reviewed to diagnose or care for the patient, or to train operators on intubation technique.

The airway images 20 acquired by the video laryngoscope 12 are visible on the laryngoscope display screen 18 that is positioned in the operator's line of sight. In addition, the acquired airway images 20 are communicated to a monitor 30, e.g., a patient vital sign monitor, a laptop, a tablet, a display screen, or other computing device. The monitor 30 also receives images from one or more environmental cameras 32 that acquire environmental images 33. The environmental images 33 are images that are acquired externally of the patient, and include contextual views of the patient and/or the environment. The environmental images may include views of the procedure room, medical clinicians such as the laryngoscope operator 13 or assisting clinicians, and other devices or medical equipment in the environment. The environmental images 33, in an embodiment, may include the video laryngoscope 12 to capture information relating to an intubation technique of the laryngoscope operator 13, which may include operator arm position, tracheal tube angle, operator pushing motions associated with advancing a tracheal tube, and/or operator use of available inputs of the video laryngoscope 12. The monitor 30 receives the airway images 20 and the environmental images 33, synchronizes them (such that they show events that happen at the same time), and generates a combined view 34 and/or a combined view video file of the synchronized images. The combined view 34 may be displayed on the monitor 30 and/or stored as a video file, e.g., with a patient record.

The monitor 30 is shown in the illustrated embodiment as a standalone and portable display positioned on a stand 36 at the patient bedside. However, the monitor 30 can be a computer, a laptop, a tablet (e.g. a tablet coupled to a portable stand), a multi-parameter patient monitor, a multifunctional medical device or instrument, a networked computer outside of the room, a mobile device, a cloud computing device in communication with a graphical user interface on a device local to an operator, or other device capable of receiving and synchronizing the airway images 20 and the environmental images 33. The monitor 30 can be positioned in the patient environment or can be a remote device. If the monitor 30 is in the room, it can also have one or more of the environmental cameras 32 mounted on/integrated on or in a housing of the monitor 30 in an embodiment.

The combined view 34 can be display on a display screen 38 integral to the monitor, streamed in real time to one or more separate display screens 35 visible to the other clinicians in the environment, and/or stored in a memory of the monitor 30 for later review. Further, the monitor 30 may or may not include the integral display 38 or the environmental camera 32.

Figure 2:
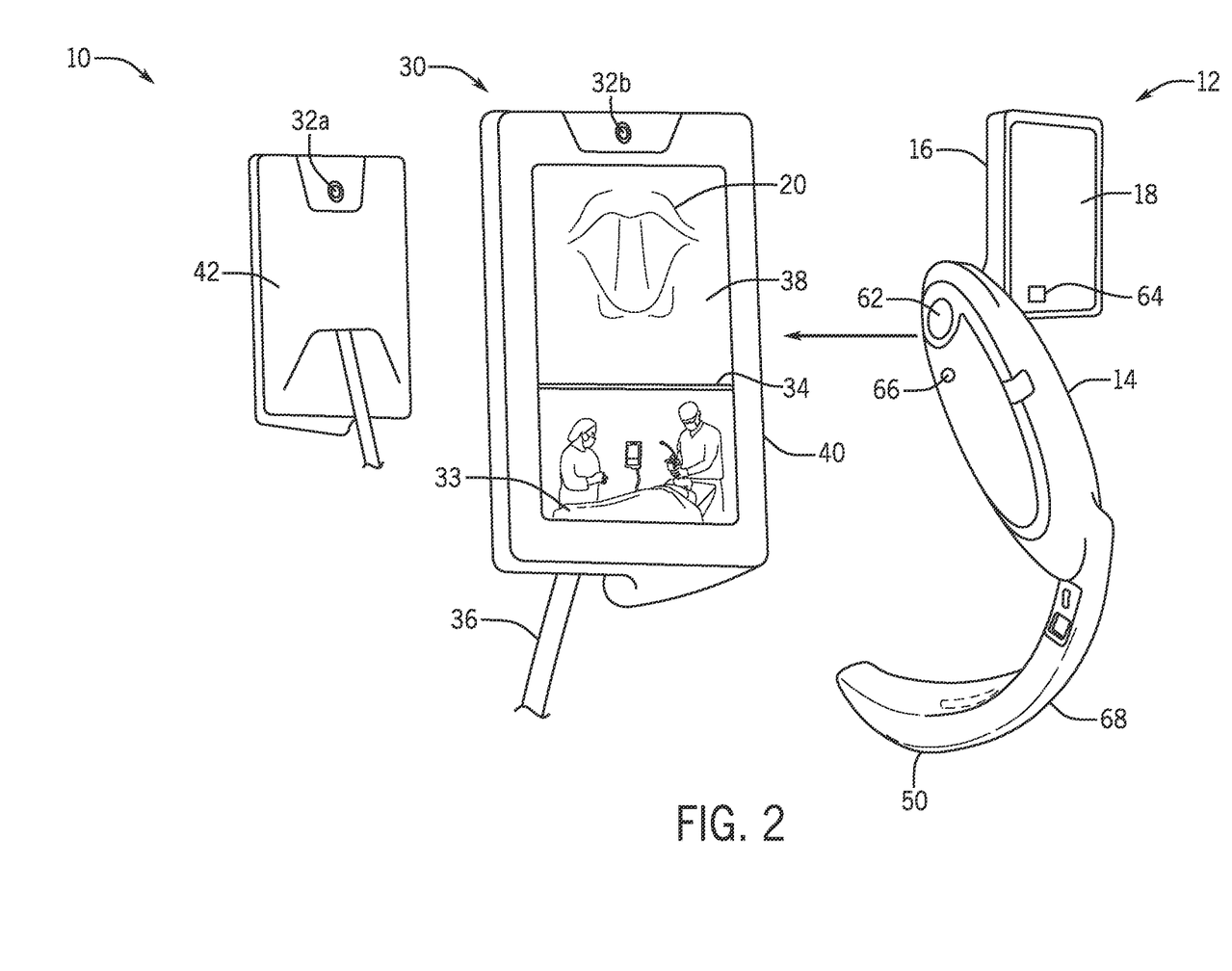
FIG. 2 is a schematic illustration of certain components of a video imaging system, in accordance with an embodiment of the present disclosure.

FIG. 2 shows an embodiment in which the camera 32 is included on a portable, upright wheeled stand 36 to capture environmental images 33. In this case, the camera 32 can be moved, e.g., wheeled, around the room so that a view of the environmental camera 32 captures a view of the patient or other desired view during an intubation or other medical procedure.

In the illustrated embodiment, the camera 32 can be an integral camera of a mobile device or tablet 40 that includes a camera assembly having a rear-facing camera 32a and/or a forward-facing camera 32b as shown. In an embodiment, the system 10 permits selection of one or both of the rear-facing camera 32a or the forward-facing camera 32b as the environmental cameras 32. The environmental camera 32 may additionally or alternatively be implemented as a portable camera, e.g., removable, web camera, or a forward-facing camera on a laptop, etc. The environmental camera 32 may be a fixed-position camera mounted in the room (such as mounted on a fixture in the room, in a corner, or on a ceiling or wall surface) or may be mounted on the portable stand 36, e.g., a wheeled stand, that includes an adjustable base to permit movement and repositioning of the environmental camera 32 to a desired position in the environment. The system 10 can, in an embodiment, detect available cameras 32 in the environment and permit activation of selected cameras and communication of acquired images to the monitor 30. For example, the system 10 can permit integration of environmental cameras 32 in a plug-and-play manner.

The tablet 40 can provide at least one environmental camera 32, e.g., as an integral camera, of the system 10 as well as display functionality via the integral display 38. For example, the display 38 can display the real-time view of the environmental images 33 to facilitate desired positioning of the camera 32. As the portable stand 36 is repositioned within the environment, the real time view of the environmental images 33 updates. The operator can adjust the stand 36 using the displayed view of the environmental images 33 as a guide for a desired field of view. The display 38 may, additionally or alternatively, display the combined view 34 generated by the monitor 30, as illustrated.

Further, in certain embodiments, the tablet 40 can perform one or more functions of the monitor 30. In one example, an operator can couple a mobile device or the portable tablet 40 to a receiving slot on the portable stand 36. The portable tablet 40 can operate as the monitor 30, such as via operation of a software application, e.g., an "app", or operation of dedicated application specific integrated circuits of the portable tablet 40. In an embodiment, one or more functions of the monitor 30 are implemented by a separate device, and the portable tablet 40 functions as the camera 32 and, optionally, a display, and communicates the captured environmental images 33 to the monitor 30.

The stand 36 may, in an embodiment, act as the monitor 30 and/or house components of the monitor 30. In this case, the stand 36 can receive the environmental and airway images, synchronize them, combine them into the combined video file, and display the combined video file 34 on the display screen 38. Thus, in an embodiment, the system 10 permits removable coupling to the environmental camera 32 and the display 38 of the tablet 40 to the stand 36, and the tablet 40 can operate as a modular or bring-your-own device component of the system 10. In one embodiment, a separate monitor 30 generates the combined view video 34 including time-aligned airway images and environmental images, and may pass the combined view video 34 to the display screen 38.

In the illustrated embodiment, the camera 32, e.g., the rear-facing camera 32a and/or a forward-facing camera 32b can be oriented to a desired view to face into the patient environment. The portable stand 36 can be maneuvered around the room on wheels, and the portable stand 36 may also include other adjustment features, such as height adjustment or tilt adjustment to tilt a housing 42 of tablet 40 and/or of the camera 32. The portable stand permits adjustment in real time if the view is obstructed as clinicians move in and out of the patient procedure field. Alternatively or additionally, the environmental images 33 can be streamed to the separate display screen 35 (see FIG. 1).

Positioning the camera 32 on the portable stand 36 permits the camera 32 to be moved to obtain a desired view at different steps or stages of a clinical procedure. By way of example, an intubation may involve fewer clinicians relative to a subsequent surgical procedure, and the desired view during the intubation procedure may be of only the torso and head region of the patient. However, the desired view during the surgical procedure may be of the whole patient and the clinicians spaced out around the patient. After the intubation, the clinicians can assume their desired positions, and the portable stand 36, and the associated camera 32, can be maneuvered to a location that captures the desired view of the patient environment during the surgical procedure and does not interfere with clinician movement. As discussed herein, the portable environment camera 32 may be one of a set of cameras 32 that capture environmental images 33.

In one example, the portable stand 36 and the portable tablet 40 stay with the patient and, if the patient is moved into a different procedure room, the portable stand 36 can be moved with the patient. Thus, the system 10 acquires environmental images 33 via the environmental camera 32 of the portable tablet 40 at various locations.

The monitor 30 of the system 10 receives the airway images 20 acquired by a camera 50 of the video laryngoscope 12 for synchronization with the environmental images 33. The airway images 20 are communicated during operation of the video laryngoscope 12, e.g., in response to actuating a power button 62 that enables a medical professional to power the video laryngoscope 12 off and on, or after interaction an input device 64 (such as a touch or proximity sensor, e.g., capacitive sensor, proximity sensor, or the like) that enables the medical professional operating the video laryngoscope 12 to provide inputs or commands.

In the illustrated embodiment, the video laryngoscope 12 may include an identifiable marker 66 that is detectable by the environmental camera 32 (e.g., based on image or feature recognition) and that is positioned on the body 14, display portion 16, and/or a blade 68 of the video laryngoscope 12 to facilitate capturing images of the patient airway entrance in the environmental images 33. The identifiable marker may include a barcode, a QR code, a fiducial, a printed symbol or text, or other camera-resolvable marker positioned in an exterior surface of the video laryngoscope 12.

In some embodiments, there may be multiple environmental cameras 32 in the environment, e.g., the patient environment, and the monitor 30 may permit user selection of one or more environmental cameras 32 to provide the environmental images that are used to generate the combined view video 34 as provided herein. While the illustrated combined view 34 includes the airway images 20 and environmental images 33 from a single camera source, the environmental images 33 may include 2, 3, or 4 video streams all put together. The multi-source environmental images 33 may be simultaneously displayed, e.g., in a gallery or panel view, in a portion of the display dedicated to the environmental images 33. In another embodiment video feeds from different environmental cameras 32 in the environment can displayed in an alternating manner that switches between different cameras based on user selection or quality metrics. For example, for a portion of a procedure, a first environmental camera 32 may provide the desired view while, in a subsequent portion of the procedure, a second environmental camera 32 provides the desired view. The operator can view the available video feeds from the environmental cameras 32 in a user interface of the monitor 30 to make selection of the desired camera view or views. The combined view 34 can be generated based on the user selection. In another embodiment, the camera feed may be selected based on identification of the identifiable marker 66 in the acquired environmental images 33. If the identifiable marker 66 is no longer resolvable, the system 10 can switch to a different environmental camera 32 until the identifiable marker 66 is visible in the environmental images 33.

Figure 3:
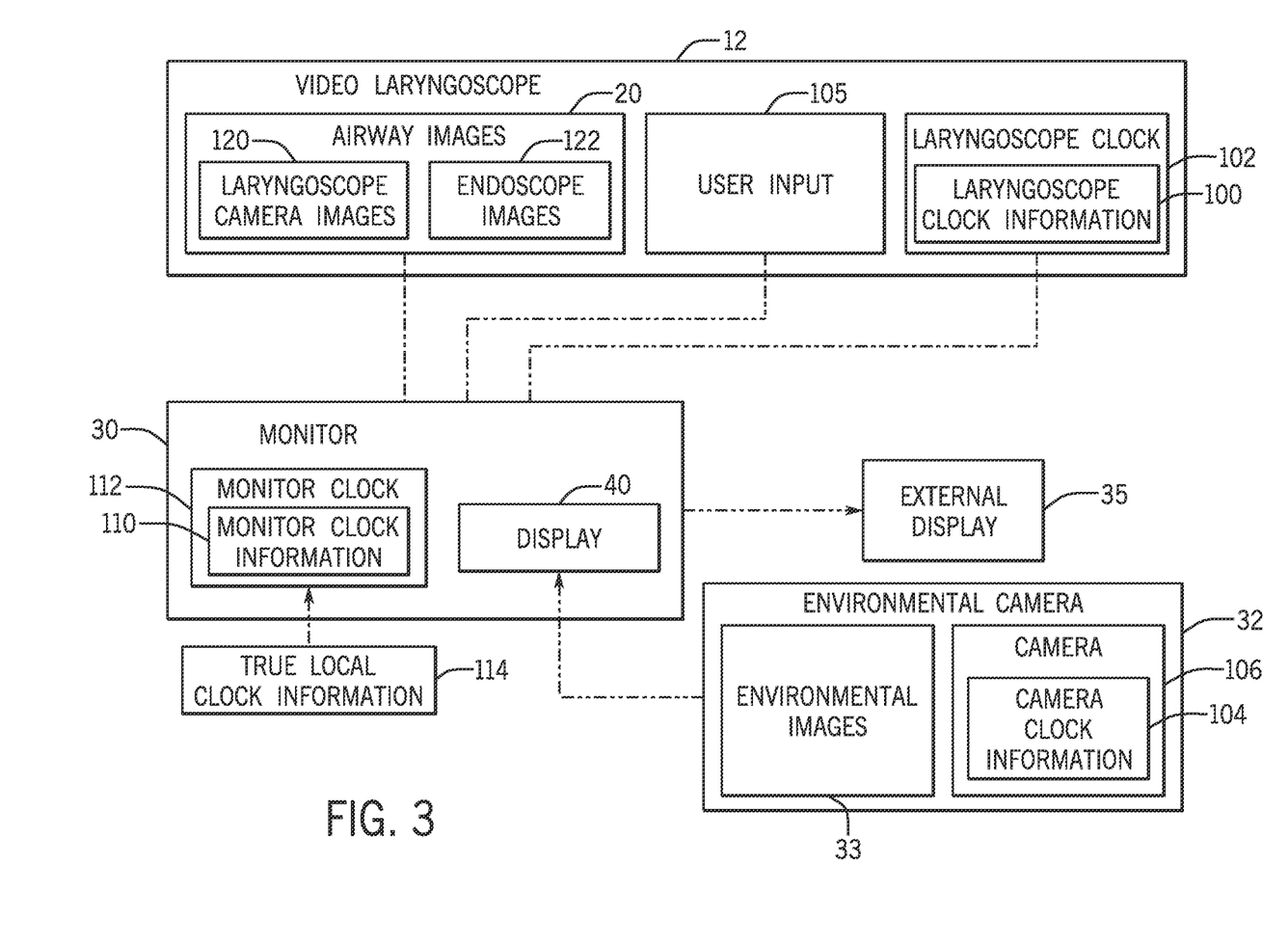
FIG. 3 is a schematic illustration of communication pathways of a video imaging system, in accordance with an embodiment of the present disclosure.

FIG. 3 is a schematic illustration of data communication pathways in the video imaging system 10 to facilitate synchronization of data from different devices, which may include acquired images and flagged events. In use, the system 10 may enable transmitting acquired airway images from the video laryngoscope 12 to one or more separate (e.g., remote) devices or systems, such as a monitor or tablet display 38 or a separate display 35), the monitor 30 (e.g., remote monitor), a computing system, and/or a hospital data storage system. For example, the video laryngoscope 12 acquires airway images that may be stored locally (e.g., in a storage device housed in the body 14) for later access, viewing, or transfer, or may be streamed in real time to the monitor 30 or other external device. In certain embodiments, the video laryngoscope 12 communicates with the monitor 30 and/or transmits data (e.g., wirelessly streams images in substantially real-time) to the monitor 30. In certain embodiments, the video laryngoscope 12 automatically transmits data from the storage device of the video laryngoscope 12 to the monitor 30 and/or transmits data to one or more other remote devices or systems at certain times (e.g., upon powering the video laryngoscope 12 and/or the monitor 30 off or on or upon receipt of a user input).

The video laryngoscope 12 and the environmental camera 32 may communicate with the monitor 30 and/or other remote devices or systems via any of a variety of techniques. For example, the video laryngoscope 12, the environmental camera 32, and the monitor 30 may include or be operatively coupled to communication devices (e.g., wireless transceivers) that establish wireless communication with one another using any suitable protocol.

The video laryngoscope 12 includes an internal laryngoscope clock 102 that generates laryngoscope clock information 100, such as time stamp information encoded with acquired image files. The laryngoscope clock information 100 is generated by the internal clock 102 on the video laryngoscope 12, which may not be set to the correct local time and/or may not match the internal clocks of other devices in the system. For example, the laryngoscope clock 102 could be set to a different time zone, could have drifted from local time by a few seconds or minutes, could be incorrect for other reasons, or could be the correct local time but still not match other devices in the system whose clocks do not match the correct local time.

In an embodiment, the video laryngoscope sends laryngoscope clock information 100, e.g., time stamp information, to the monitor 30. This could be a single time at the start or end of a video file, a time in the middle of the video file, a start time plus a duration of the video, ongoing time stamps throughout the video, e.g., at each image frame, or other time information that associates the acquired airway images 20 with the laryngoscope's clock 102.

The laryngoscope clock information 100, and any associated data, is communicated to the monitor 30 via communication pathways disclosed herein. In one example, the user may initiate recording or transmitting of airway images with an initiating or calibrating user input 105 (e.g., actuating a thumb-operable control) that includes laryngoscope clock information 100 associated with a time of the user input. During an intubation, the laryngoscope operator may also provide a patient event flag via the user input 105 associated with a patient event, such as coughing or patient movement, that may be relevant to an analysis of the intubation procedure. The patient event flag may include time stamp information generated by the laryngoscope clock 102.

During the intubation, the environmental camera 32 also records video images. The environmental camera 32 also includes a local camera clock 106 which may or may not match the true or absolute local time per standard local clock information 114. The environmental camera 32 sends environmental camera clock information 104 to the monitor 30. The monitor 30 then uses the local clock information from each contributing device—the laryngoscope clock information 100 and the environmental camera clock information 104—to align the airway video and the environmental video to a synchronized time, so that events occurring in the room and with the patient happen at the same time in each video.

In embodiments in which the environmental camera 32 is integral with the monitor 30, the camera clock information 104 is the same as the monitor clock information 110, and the monitor 110 does not necessarily receive separate camera clock information 104 from the environmental camera 32. That is, the system 10 includes at least the video laryngoscope clock 102 and one or both of the environmental camera clock 106 or the monitor clock 112. It should be understood that the disclosed synchronization may be relative synchronization to the monitor 30 in which the monitor clock 112 is the controlling time, regardless of whether the monitor clock 112 corresponds to the true local clock information 114. In other embodiments, the synchronization is set to the true local clock information 114 received by the monitor 30, which in turn sets the monitor clock 112.

In an embodiment, the monitor receives the airway video images 20 that include laryngoscope clock information 104 and the environmental video images 33 that include camera clock information 104. The monitor 30 can automatically query the video laryngoscope 12 for a current time per the laryngoscope clock 102, which the video laryngoscope 12 sends to the monitor 102. Alternatively, the video laryngoscope can send the current time without a monitor query to initiate synchronization. The monitor 30 determines a first time discrepancy or first delta time between monitor clock time and the video laryngoscope clock time in response. When the environmental camera 32 has a separate clock 106, the monitor 30 queries the environmental camera 32 for its current time. In response to receiving the current time from the camera clock 106, the monitor 30 determines a second time discrepancy or second delta time between the monitor time and the environmental clock time. Accordingly, the monitor 30 is able to correct both video image streams to the monitor's time, and synchronize them.

Figure 4:
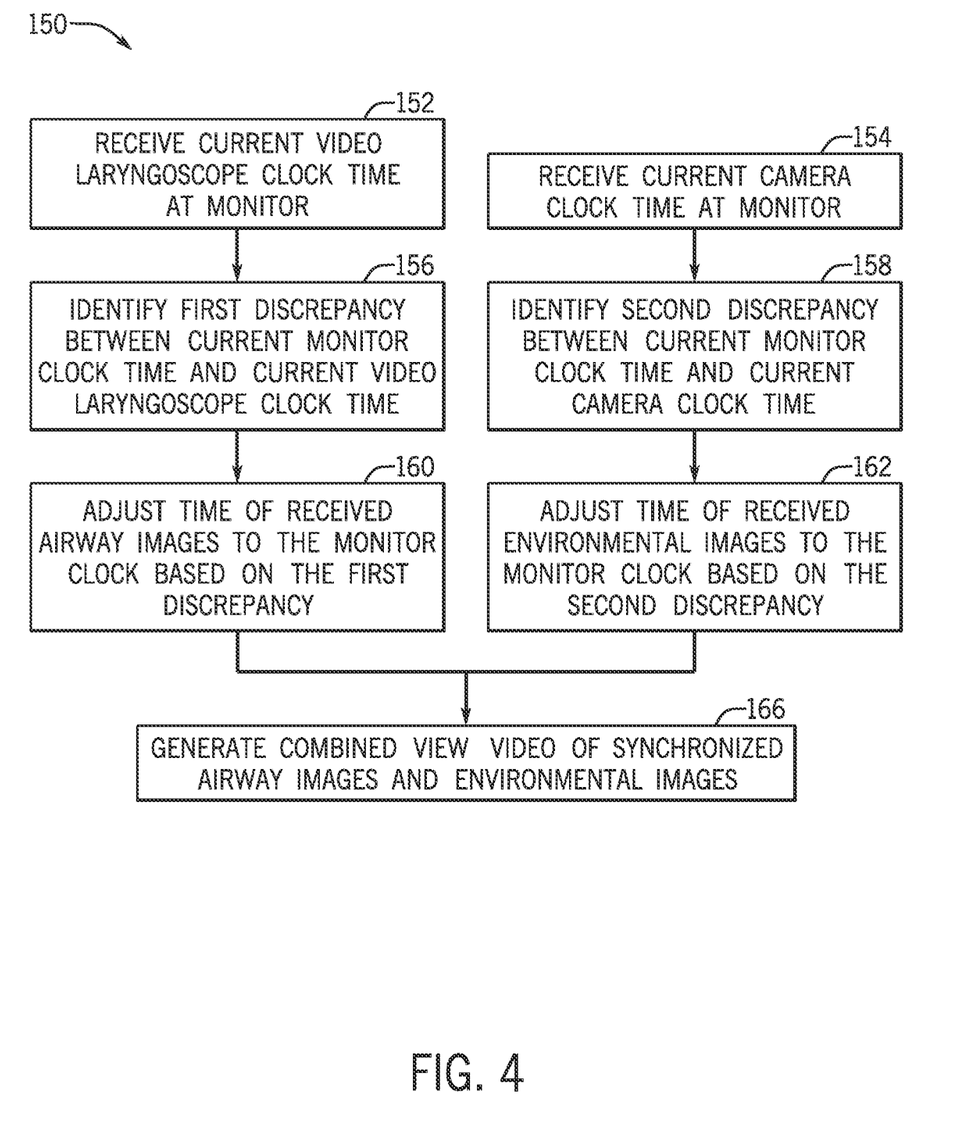
FIG. 4 is a flow diagram of a method used in conjunction with a video imaging system, in accordance with an embodiment of the present disclosure.

FIG. 4 is a process flow diagram of a method 150 of using the laryngoscope system 10 and with reference to features discussed in FIGS. 1-3, in accordance with an embodiment of the present disclosure. The method 150 disclosed herein includes various steps represented by blocks. It should be noted that at least some steps of the method 150 may be performed as an automated procedure by a system, such as the system 10. Although the flow chart illustrates the steps in a certain sequence, it should be understood that the steps may be performed in any suitable order and certain steps may be carried out simultaneously, where appropriate. Additionally, steps may be added to or omitted from of the method 150. Further, certain steps or portions of the method 150 may be performed by separate devices. For example, a portion of a method 150 may be performed by the video laryngoscope 12, while other portions of the method 150 may be performed by an environmental camera 32 or a processor of the monitor 30. In addition, insofar as steps of the method 150 disclosed herein are applied to images, it should be understood that the images may be image data, processed images, or image files and may be still images or video images.

The method 150 initiates with the monitor receiving a current video laryngoscope time at the monitor (block 152). In certain embodiments, where the environmental camera 32 does not share the monitor clock 112, the method 150 includes receiving a current camera clock time at the monitor (block 154). The current laryngoscope clock time reflects the time at the video laryngoscope 12 that is sent in response to a query from the monitor or automatically from the video laryngoscope 12 as part of initiation of communication with the monitor 30. The monitor 30 may compare the current laryngoscope clock time to the current monitor clock time to identify a first discrepancy (block 156), e.g., a delta time, reflective of the respective clock differences between the monitor 30 and the video laryngoscope 12 at a given time point and compare the current camera clock time to the current monitor clock time to identify a second discrepancy (block 156), e.g., a second delta time, reflective of the respective clock differences between the monitor 30 and the environmental camera 32 at a given time point. As disclosed herein, the environmental camera 32 may be integrated with or hard-wired to the monitor 30, and, therefore, may share the monitor clock 112. In such cases, there will be no discrepancy between the camera clock time and the monitor clock time, and certain image time-synchronization steps may be omitted in the method 150.

The monitor 30 adjusts the time associated with received airway images 20 from the video laryngoscope 12 based on the identified first discrepancy (block 160). Adjusting the time may include shifting the time stamp information associated with the received airway images 20 to synchronize with the monitor clock time. The monitor 30 may also adjust the time associated with received environmental images 33 from the environmental camera 32 based on the identified second discrepancy (block 162) so that the time is shifted to synchronize with the monitor clock time. The monitor 30, in operation, generates a combined or composite view video of the time-aligned airway images and environmental images (block 166). The monitor 30 provides a relative reference to which both image streams can be adjusted or shifted. If frame rates of the different cameras differ, the frames can be interpolated to bring them together into the combined video file. The monitor uses the relative difference between the monitor/video laryngoscope and, if present, the monitor/environmental camera 32 to align the two image streams together. Once aligned, the image streams can run forward together.

The combined view video may include successive combined views 34 in which each combined view is a frame of the airway images 20 displayed together with a frame of the environmental images 33 that was acquired at the same absolute time point or the same time point according to the monitor clock 112. The combined view video may be automatically displayed as it is being generated, or may be generated and stored in a memory for later playback. Further, the combined view video may be generated in real time or based on previously acquired airway images 20 and environmental images from a simultaneous time window.

Figure 5:
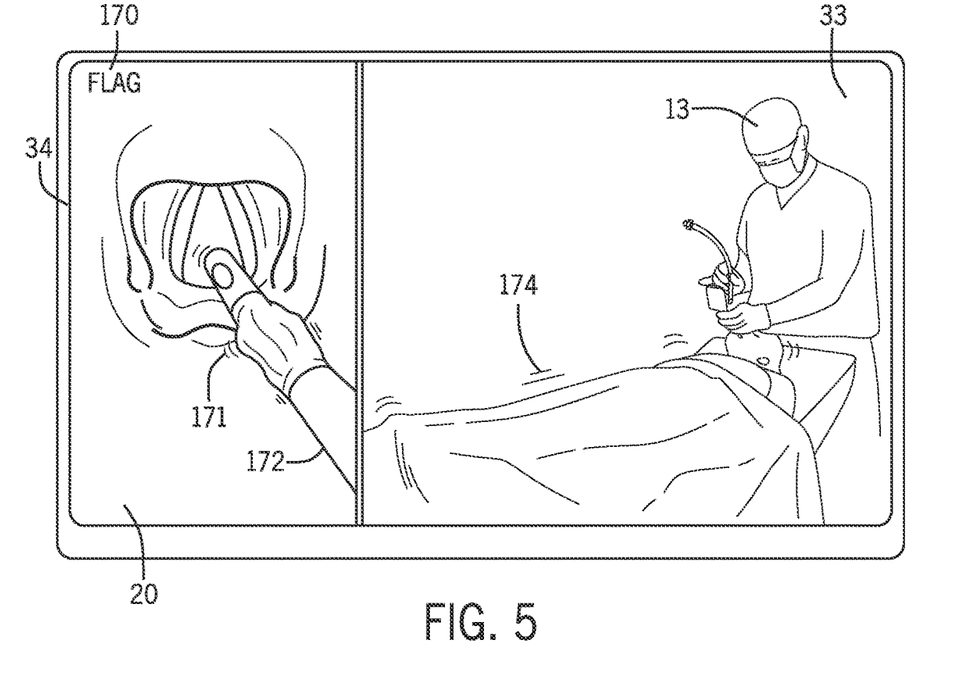
FIG. 5 is an example display screen showing a combined view of airway images and environmental images, in accordance with an embodiment of the present disclosure.
Figure 6:
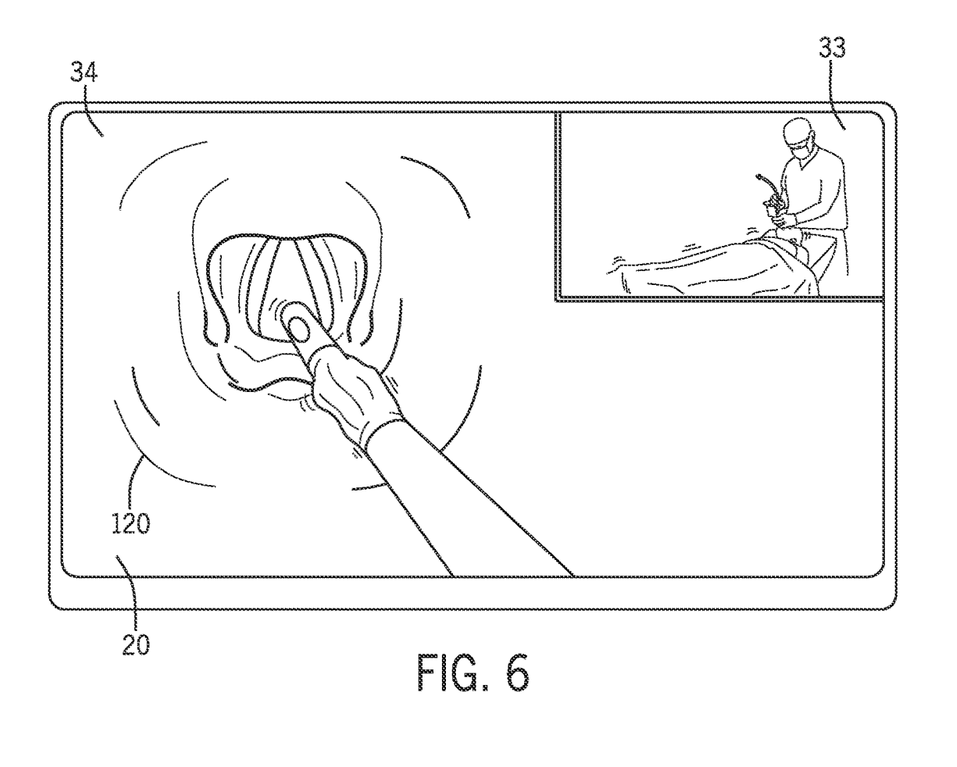
FIG. 6 is an example display screen showing a combined view of airway images and environmental images, in accordance with an embodiment of the present disclosure.

FIG. 5 is an example display of a frame of combined view 34 as provided herein showing airway images 20 in a side-by-side arrangement with the environmental images 33. It should be understood that other arrangements are also contemplated, such as a top-bottom arrangement, an overlay arrangement, or a picture-in-picture arrangement, as shown in FIG. 6. Turning back to FIG. 5, in the depicted example, the frame of the combined view 34 is annotated with a patient event flag 170, e.g., that may be flagged at a particular time or within a time window. For example, the patient event flag 170 may be a result of a user input, e.g., a thumb-operable control, indicating a patient movement, represented by dashed lines indicating movement relative to previous frames. The patient movement may be evident in the airway images by a shifting 171 of an advancing tracheal tube 172 within the airway, while the patient movement 174 may also be seen in a macro view in the environmental images 33. Reviewing a video file showing the combined view 34 may reveal a cause of the patient movement, such as coughing, intervention by the laryngoscope operator 13 or other clinicians, or insufficient sedation. The combined view 34 may also include a timer indicator that is set to a start of a procedure.

FIG. 6 shows an alternate implementation of the combined view 34 as provided herein showing environmental images 33 embedded in a larger view of the airway images 20. It should be understood that other arrangements are also contemplated, such as a top-bottom arrangement, an overlay arrangement, or a picture-in-picture arrangement, as shown in FIG. 6. Turning back to FIG. 5, in the depicted example, the frame of the combined view 34 is annotated with a patient event flag 170, e.g., that may be flagged at a particular time or within a time window. For example, the patient event flag 170 may be a result of a user input, e.g., a thumb-operable control, indicating a patient movement, represented by dashed lines indicating movement relative to previous frames. The patient movement may be evident in the airway images by a shifting of an advancing tracheal tube 172 within the airway, while the patient movement may also be seen in a macro view in the environmental images 33. Reviewing a video file showing the combined view 34 may reveal a cause of the patient movement, such as coughing, intervention by the laryngoscope operator 13 or other clinicians, or insufficient sedation. The combined view 34 may also include a timer indicator that is set to a start of a procedure.

Figure 7:
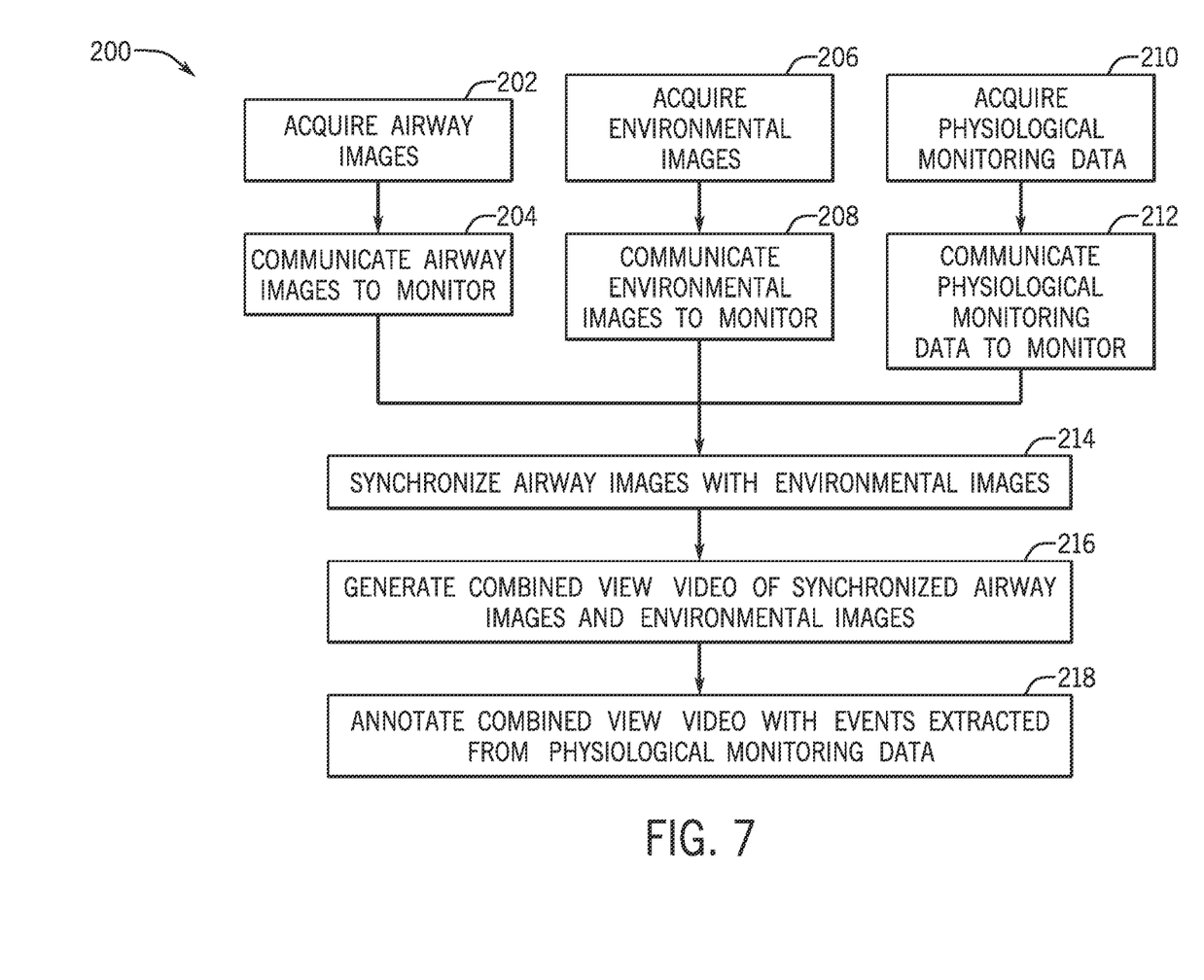
FIG. 7 is a flow diagram of a method used in conjunction with a video imaging system, in accordance with an embodiment of the present disclosure.

FIG. 7 is a process flow diagram of a method 200 of using the laryngoscope system 10 of FIG. 1, in accordance with an embodiment of the present disclosure. The method 200 disclosed herein includes various steps represented by blocks. It should be noted that at least some steps of the method 200 may be performed as an automated procedure by a system, such as the system 10. Although the flow chart illustrates the steps in a certain sequence, it should be understood that the steps may be performed in any suitable order and certain steps may be carried out simultaneously, where appropriate. Additionally, steps may be added to or omitted from of the method 200. Further, certain steps or portions of the method 200 may be performed by separate devices. For example, a portion of a method 200 may be performed by the video laryngoscope 12, while other portions of the method 200 may be performed by the environmental camera 32, physiological sensors, or a processor of the monitor 30. In addition, insofar as steps of the method 200 disclosed herein are applied to images, it should be understood that the images may be image data, processed images, or image files and may be still images or video images. In addition, insofar as steps of the method 200 disclosed herein are applied to physiological monitoring data, it should be understood that the monitoring data may be raw data or processed data.

The method 200 initiates with the video laryngoscope 12 acquiring airway images (e.g., airway images 20, FIG. 1) (block 202) and communicating the airway images to the monitor 30 (block 204). At the same time as the airway images are acquired, the environmental camera 32 acquires environmental images (e.g., environmental images 33, FIG. 1) (block 206) that show the environment of the patient. Physiological monitoring data is acquired by one or more medical sensors (block 210) and communicated to the monitor 30 (block 212). This data can include physiologic parameters of the patient, such as vital signs like pulse rate, oxygen saturation, respiratory rate, temperature, blood pressure, and other parameters. The monitor 30 synchronizes the airway images 20 with the environmental images 33 (block 214) as provided herein to generate a combined view video 34 (block 216). The combined view video 34 is annotated with events extracted from the physiological monitoring data (block 218). The monitor 30 may synchronize the physiological monitoring data to the synchronized airway images 20 and environmental images 33 so that the physiological monitoring events are annotated at a time of occurrence on the combined view 34. The synchronization of the physiological monitoring data can occur in a manner similar to that disclosed with respect to the video laryngoscope 12 and/or the environmental camera 32 based on discrepancies between a clock of a physiological monitoring device that communicates sensor data and the monitor 30.

In one example, the annotation is based on monitoring data outside of preset tolerances. Accordingly, the monitor 30 may identify time periods associated with deviations in a physiological parameter, and annotates the combined view 34 to indicate that a deviation is occurring concurrent with a particular portion of the combined view 34.

Figure 8:
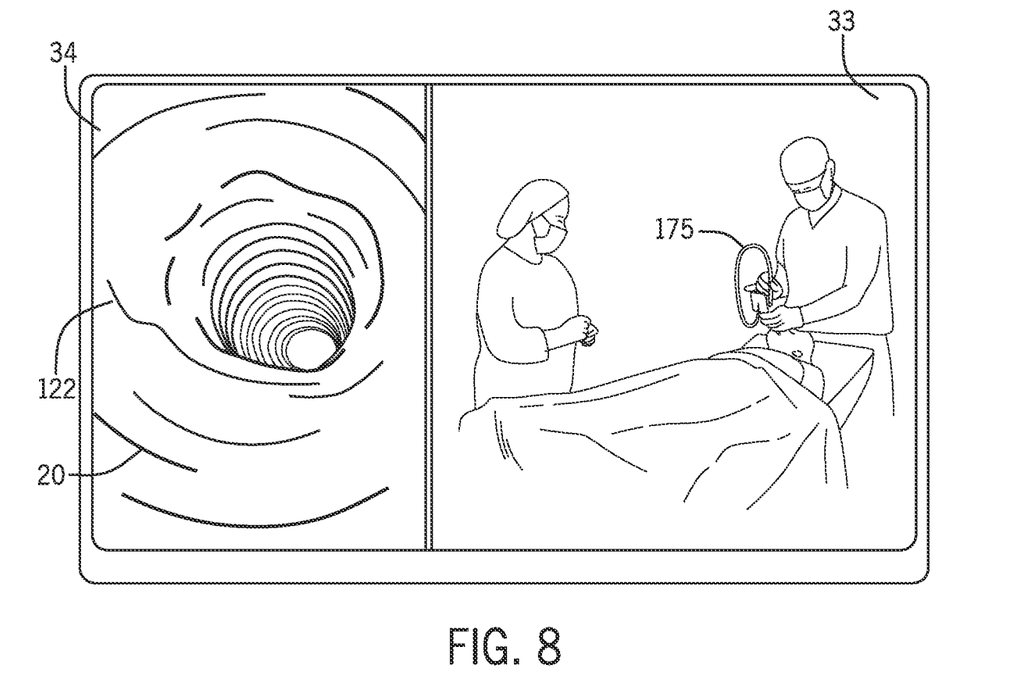
FIG. 8 is an example display screen showing a combined view of airway images and environmental images, in accordance with an embodiment of the present disclosure.

In an embodiment, the system may also include an endoscope 175 (see FIG. 8). The endoscope 175 may be a separate device that sends images to the monitor 30, or the endoscope 175 may be coupled to the video laryngoscope 12 and may send images to the video laryngoscope, which then sends them to the monitor. When the endoscope 175 is coupled to the video laryngoscope, the airway images 20 acquired by the video laryngoscope and sent to the monitor may be a combination of both the laryngoscope camera images 120 and endoscope images 122 together in one video file, in which case the endoscope images 122 are aligned with the video laryngoscope clock information. Alternatively, the endoscope images 122 may be sent separately to the monitor 30 along with endoscope clock information from the endoscope 175. The combined view 34 maybe generated with one or both of the laryngoscope camera images 120 and endoscope images 122.

FIG. 8 is an example display of an embodiment in which the combined view 34 uses an endoscopic airway images 20 from an endoscope that is coupled to the video laryngoscope 12. The endoscope 175 may be advanced into the patient airway to capture endoscopic airway images 20 that are provided to the coupled video laryngoscope 12. The video laryngoscope 12 may be capable of displaying the laryngoscope camera images from the laryngoscope camera 50, the endoscope images from the endoscope camera, or both on the display 18, and may alternate between display modes based on user input at the video laryngoscope 12. Accordingly, the video laryngoscope 12 can provide two sets of airway images 20 to the monitor 30. A first set of images includes the laryngoscope camera images 120 and a second set includes the endoscope images 122 (FIG. 3). Each set of images is associated with clock information (such as both being associated with the laryngoscope clock information, or the laryngoscope images 120 being associated with laryngoscope clock information and the endoscope images 122 being associated with endoscope clock information) that is used to synchronize the images into the combined video file as disclosed herein.

Figure 9:
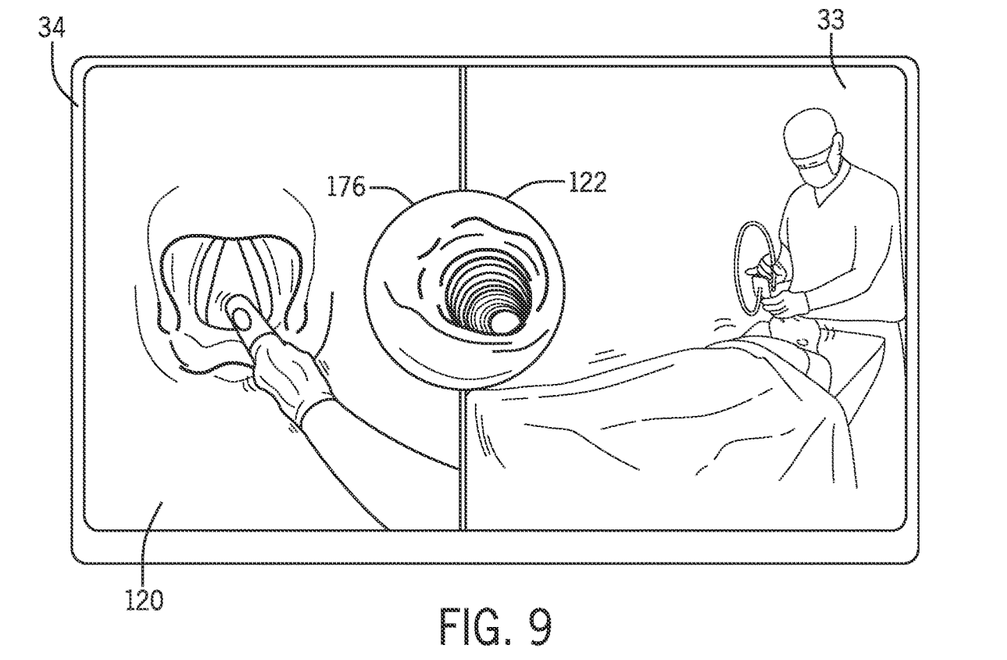
FIG. 9 is an example display screen showing a combined view of airway images and environmental images, in accordance with an embodiment of the present disclosure.

The combined view 34 may be generated based on the images from the laryngoscope camera 50 and/or the endoscope images 122. While the display 18 of the video laryngoscope 12 may toggle between alternating displays of the laryngoscope camera images 120 and the endoscope images 122, the video laryngoscope 12 may display one or both of the respective images. Further, any of the images may be overlaid on top of the others in the combined video file. For example, FIG. 9 is an example display of the combined view 34 in which the endoscope images 122 are overlaid atop both the laryngoscope camera images 120 and the environmental images 33. The system 10 may permit the user to toggle the overlay images to be between the endoscope images 122 and the laryngoscope camera images 120, such as by swiping one image to the other image to switch them. In an embodiment, the display panel or outline 176 of the endoscope images 122 may be shown as a circle or different shape relative to other displayed images in a manner consistent with a display mode of the video laryngoscope 12 to create continuity with the display style of the video laryngoscope 12.

Figure 10:
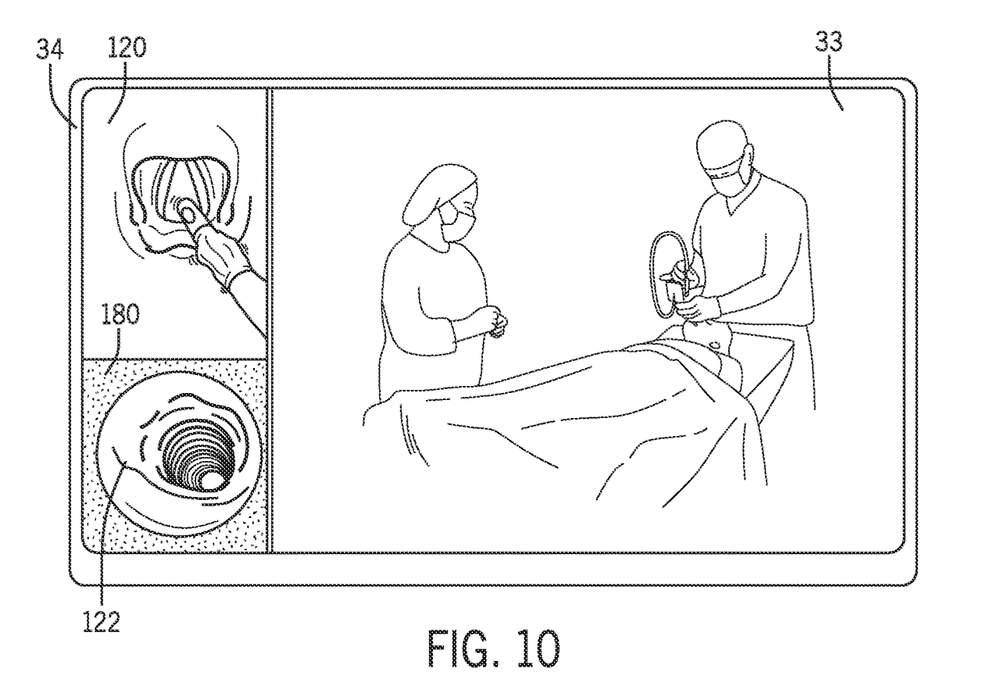
FIG. 10 is an example display screen showing a combined view of airway images and environmental images, in accordance with an embodiment of the present disclosure.

FIG. 10 is an alternative combined view 34 showing a multi-panel arrangement in which the laryngoscope camera images 120 are arranged in a first panel, the endoscope images 122 are arranged in a second panel, and the environmental images 33 are arranged in a third panel of the combined view 34. The endoscope images 122, as discussed with respect to FIG. 9, may be displayed with display settings to maintain a particular shape (e.g., circle). Further, a background color 180 or outline surrounding a panel, such as the panel displaying the endoscope images 122, may be different relative to other panels for ease of distinction between various images. In an embodiment, the relative positions and sizes of these panels may be adjusted via settings of the video imaging system 10. Further, one or more panels may be eliminated. In one example, if an endoscope is not coupled to the video laryngoscope 12, such that no endoscope images 122 are received by the monitor 30, the combined view 34 automatically omits any dedicated panel for the endoscope images 122. Coupling of the endoscope to the video laryngoscope 12 and receipt of endoscope images 122 by the monitor 30 triggers activation of the appropriate display panel on the combined view 34.

Figure 11:
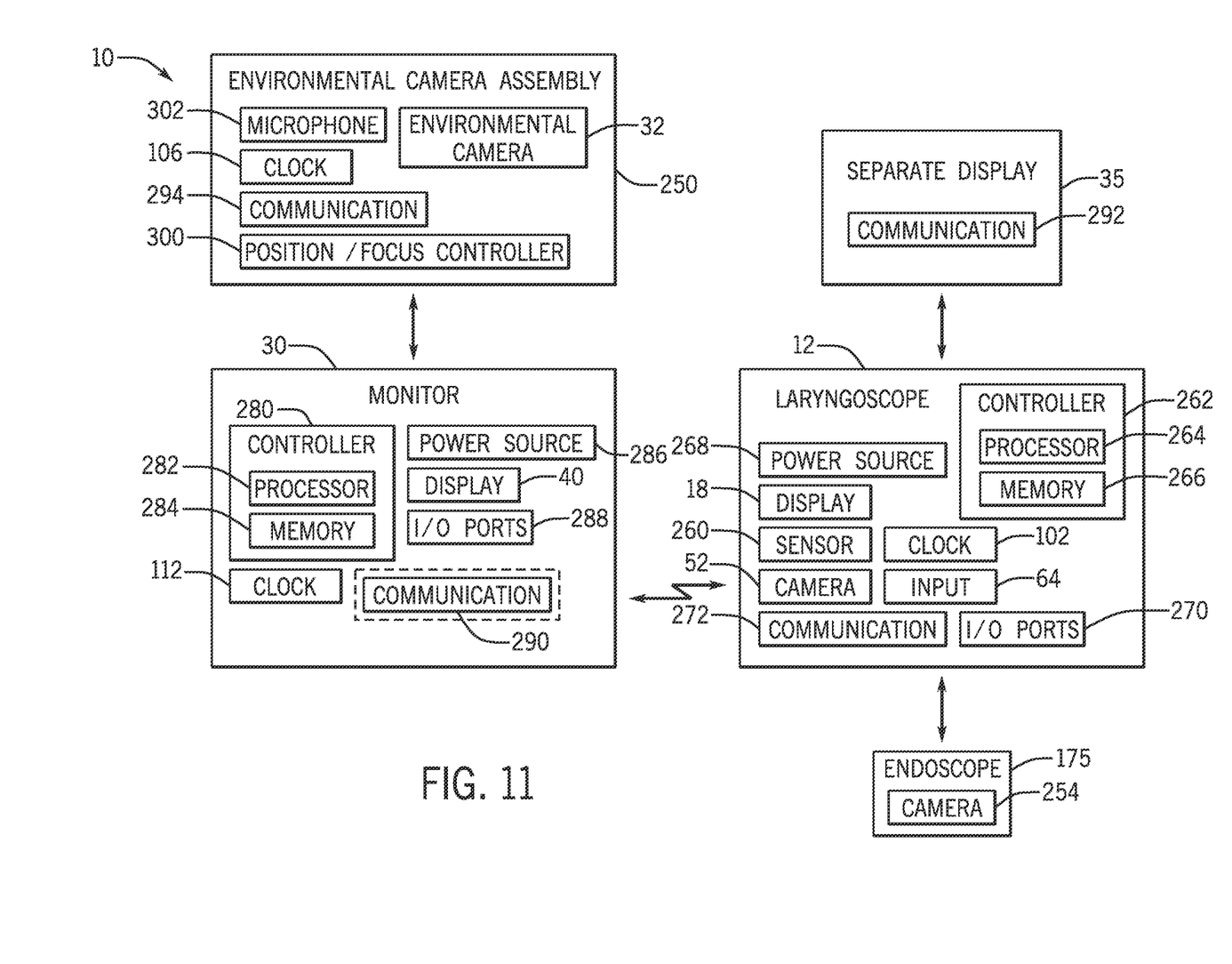
FIG. 11 is a block diagram of a video imaging system, in accordance with an embodiment of the present disclosure.

FIG. 11 is a block diagram of an embodiment of the video imaging system 10. As shown, the system 10 includes the video laryngoscope 12 and the monitor 30. Further, the system 10 includes an environmental camera assembly 250 that includes the environmental camera 32. In certain embodiments, the video laryngoscope 12 is coupled to an endoscope 175 with an integral endoscope camera 254.

The video laryngoscope 12 and the monitor 30 may include various components that enable the system 10 to perform the techniques disclosed herein. For example, the video laryngoscope 12 may include the display screen 18, the camera 50, coupled sensors 260, and the input (e.g., touch sensor) 64, as well as a controller 262 (e.g., electronic controller), one or more processors 264, a hardware memory 266, a power source (e.g., battery) 268, input/output (I/O) ports 270, a communication device 272, and a laryngoscope clock 102 that generates laryngoscope clock information 100 (FIG. 3).

The monitor 30 may include the display screen 54, a controller 280 (e.g., electronic controller), one or more processors 282, a hardware memory 284, a power source (e.g., battery or input from external power source) 286, I/O ports 288, and a communication device 290. The power sources 268, 286 may be rechargeable and/or replaceable batteries. The communication devices 272, 290 and other communication devices of the system 10, such as a communication device 292 of the separate display 22 or a communication devices 294 of the environmental camera assembly 250 may be wireless transceivers that are configured to establish wireless communication with one another. By way of example, the communication devices may be configured to communicate using the IEEE 802.15.4 standard, and may communicate, for example, using ZigBee, WirelessHART, or MiWi protocols. Additionally or alternatively, the communication devices may be configured to communicate using the Bluetooth standard or one or more of the IEEE 802.11 standards. As noted above, in some embodiments, the communication device 268 may be provided in the adapter 70 that is configured to couple to the monitor 30 to facilitate wireless communication between the video laryngoscope 12 and the monitor 30. The monitor 30 also include a monitor clock 112 that generates monitor clock information 110 (FIG. 3).

In certain embodiments, the video laryngoscope 12 and the monitor 30 include electrical circuitry configured to process signals, such as signals generated by the camera 50, signals generated by the environmental camera 32, and/or control signals provided via inputs to the monitor 30, or the input 64 on the video laryngoscope 12, for example. In the illustrated embodiment, the processors 264, 282 may be used to execute software. For example, the processor 264 of the video laryngoscope 12 may be configured to receive signals from the camera 50 and the endoscope 175, when coupled, and to execute software to generate an image and/or to carry out any of a variety of processes in accordance with the present disclosure (e.g., display the image, store the image, transfer the image, or the like). The processor 282 of the monitor 30 may be programmed to generate the combined view 34 as provided herein and to synchronize the airway images 20 and the environmental images 33. Moreover, the processors 264, 282 may include multiple microprocessors, one or more "general-purpose" microprocessors, one or more special-purpose microprocessors, and/or one or more application specific integrated circuits (ASICS), or some combination thereof. For example, the processors 264, 282 may include one or more reduced instruction set (RISC) processors. It should be appreciated that the various processing steps may be carried out by either processor 264, 282 or may be distributed between the processors 264, 282 in any suitable manner.

The hardware memory 266, 284 may include a volatile memory, such as random access memory (RAM), and/or a nonvolatile memory, such as read-only memory (ROM). It should be appreciated that the hardware memory 266, 284 may include flash memory, a hard drive, or any other suitable optical, magnetic, or solid-state storage medium, other hardware memory, or a combination thereof. The memory 266, 284 may store a variety of information and may be used for various purposes. For example, the memory 266, 284 may store processor-executable instructions (e.g., firmware or software) for the processors 264, 282 to execute, such as instructions for processing signals generated by the camera 50 to generate the image, provide the image on the display screen 18, and/or transmit the image to the monitor 30. The hardware memory 266, 284 may store data (e.g., previously obtained images, time data, etc.), instructions (e.g., software or firmware for generating the images, storing the images, transmitting the images, etc.), and any other suitable data.

The system 10 may include features for automatically adjusting a position or focus of the environmental camera 32. The environmental camera assembly may include a position/focus controller that executes commands to adjust a field of view of the environmental camera. For example, the monitor 30 or the controller 300 may process environmental images 32 using object recognition techniques to identify the identifiable marker 66 (FIG. 2) that is disposed on the video laryngoscope and adjust the camera position so that the identifiable marker 66 is retained (such as keeping it centered) within the field of view.

The environmental camera assembly 250 also includes a microphone 302 to capture environmental sounds, which may include clinician instructions, patient sounds, and medical device alarms, and include the microphone-captured data synchronized with the environmental images 33 so that the combined view 34 includes audio. As discussed herein, the environmental camera 32 may be hardwired to the monitor 30 to receive clock information from the monitor clock 112. However, the environmental camera assembly may include an integral clock 106 that generates clock information associated with the acquired environmental images 33.

Because patients that require mechanical ventilation may have complex and overlapping medical conditions, the combined view video file generated by the video imaging system facilitates review or analysis of an intubation procedure with additional environmental context. Intubation success to rapidly and effectively secure the patient airway may be related to the skill and training of the intubator and assisting clinicians, the familiarity of the clinicians with the available equipment, the internal airway anatomy, and the patient's clinical condition. The disclosed techniques permit more accurate review of an intubation procedure by providing the environmental context in a user-friendly display configuration that accounts for device-specific differences in internal clock information. The accurate review may lead to more accurate characterization of contributing factors to difficult or failed intubations, which in turn may improve patient care. The disclosed techniques solve problems of discrepancies between clocks of coupled devices to facilitate synchronization of images acquired by the un-synchronized devices.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that certain elements of the disclosed embodiments may be combined or exchanged with one another.

What is claimed is:

1. A video imaging system, comprising:
a monitor comprising a display screen;
a video laryngoscope comprising a camera that acquires airway images of a patient; and
an environmental camera that acquires environmental images of a patient environment;
wherein the monitor operates to:
receive the airway images from the video laryngoscope and the environmental images from the environmental camera;
receive a video laryngoscope clock time from the video laryngoscope;
determine a first difference between the video laryngoscope clock time and a monitor clock time;
synchronize the airway images and the environmental images based on the first difference; and
combine the synchronized airway and environmental images into a combined video file.

2. The video imaging system of claim 1, wherein the combined video file comprises a side-by-side view of the synchronized airway images and environmental images.

3. The video imaging system of claim 1, wherein the monitor operates to use the first difference to synchronize the airway images to the monitor clock time.

4. The video imaging system of claim 1, wherein the monitor operates to receive an environmental camera clock time from the environmental camera and determine a second difference between the environmental camera clock time and the monitor clock time.

5. The video imaging system of claim 4, wherein the monitor operates to use the second difference to synchronize the environmental images to the monitor clock time.

6. The video imaging system of claim 1, wherein the environmental camera is housed in or on the monitor.

7. The video imaging system of claim 1, wherein the monitor comprises a portable tablet.

8. The video imaging system of claim 7, wherein the environmental camera is coupled to the portable tablet on a side opposite the display screen.

9. The video imaging system of claim 1, wherein one or both of the monitor or the environmental camera is coupled to a portable stand.

10. The video imaging system of claim 1, wherein the monitor operates to:
identify the video laryngoscope in the environmental images; and
adjust a field of view of the environmental camera to retain the video laryngoscope in the field of view.

11. A medical device system comprising:
a video laryngoscope that acquires airway images of a patient;
an environmental camera that acquires environmental images;
a monitor that operates to:
receive the airway images from the video laryngoscope;
receive the environmental images from the environmental camera;
determine a first time difference between a monitor clock and a video laryngoscope clock, and a second time difference between the monitor clock and an environmental camera clock;
shift the airway images relative to the environmental images based on the first and second differences, to time-synchronize the airway images and the environmental images to each other; and
generate a video file comprising the time-synchronized airway images and environmental images.

12. The medical device system of claim 11, wherein the environmental camera is mounted to a portable stand.

13. The medical device system of claim 11, wherein the monitor receives the airway images wirelessly and in real time.

14. A method, comprising:
receiving, at a monitor, airway images and laryngoscope clock information from a video laryngoscope;
acquiring, by the monitor, environmental images from a room-facing environmental camera on the monitor, wherein the environmental images are acquired simultaneously with the airway images;
determining a relative time difference between the laryngoscope clock information and a monitor clock information;
time-synchronizing the airway images and the environmental images based on the relative time difference; and
generating a composite video file with a combined view of the time-synchronized airway images and environmental images.

15. The method of claim 14, wherein the composite video file includes a picture-in-picture or a side-by-side view.

16. The method of claim 14, wherein the environmental images are time-stamped with monitor clock information.

17. The method of claim 14, further comprising:
receiving, at the monitor, endoscopic images and endoscope clock information from an endoscope;
determining a second relative time difference between the endoscope clock information and the monitor clock information; and
time-synchronizing the endoscopic images with the environmental images based on the second relative time difference,
wherein the combined view in the composite video file further includes the time- synchronized endoscopic images.

18. The method of claim 14, further comprising:
receiving patient vital sign data from a patient monitor;
identifying a patient event and an associated time of the patient event in the patient vital sign data; and
overlaying information indicative of the patient event onto the composite video file at the associated time.

19. The method of claim 14, further comprising displaying the composite video file on a display screen of the monitor.

20. The method of claim 14, further comprising storing the combined video file with a patient record.

* * * * *